United States Patent [19]

Li Bassi et al.

[11] Patent Number: 4,908,398

[45] Date of Patent: Mar. 13, 1990

[54] POLY 1,4-DIHYDRO-2,6-DIMETHYLPYRIDINE-3,5-DICARBOXYLESTERS USEFUL AS THERMAL STABILIZERS FOR SYNTHETIC POLYMERS

[75] Inventors: Giuseppe Li Bassi, Gavirate; Roberto Ortica, Legnano, both of Italy

[73] Assignee: Lagor S.p.A., Italy

[21] Appl. No.: 174,864

[22] Filed: Mar. 29, 1988

[30] Foreign Application Priority Data

Apr. 15, 1987 [IT] Italy .................. 20128 A/87

[51] Int. Cl.$^4$ ............ C07D 213/55; C08K 5/34
[52] U.S. Cl. ................... 524/99; 524/104; 524/105; 546/249; 546/263
[58] Field of Search ............ 546/249, 263; 524/99, 524/104, 105

[56] References Cited

U.S. PATENT DOCUMENTS

| | | | |
|---|---|---|---|
| 3,939,171 | 2/1976 | Meyer et al. | 546/263 |
| 4,214,088 | 7/1980 | Abeler et al. | 524/99 |
| 4,239,893 | 12/1980 | Pigerol et al. | 524/99 |
| 4,317,768 | 3/1982 | Pigerol et al. | 524/99 |
| 4,515,916 | 5/1985 | Molt | 524/99 |

FOREIGN PATENT DOCUMENTS

| | | |
|---|---|---|
| 1179342 | of 0000 | Canada . |
| 0051334 | 5/1982 | European Pat. Off. . |
| 2437422 | 4/1980 | France . |

*Primary Examiner*—Veronica P. Hoke
*Attorney, Agent, or Firm*—Arnold, White & Durkee

[57] ABSTRACT

Poly-dihydro-2,6-dimethylpyridine-3,5-dicarboxylesters of general formula (I)

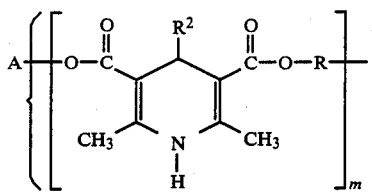

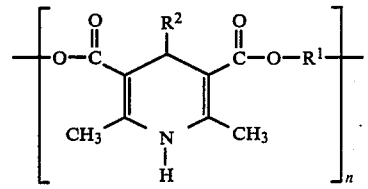

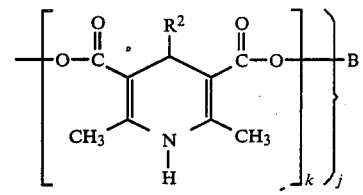

in which A, B, m, n, k, j, R, $R^1$ and $R^2$ have the meanings defined in the text, useful as thermal stabilizers for synthetic polymers, in particular for polyvinylchloride-based masses.

The compounds of formula (I) are preferably used in combination with the usual stabilizers based on organic metal derivatives. They can also be used combined with agents which exert a synergic action in maintaining a low color of manufactured articles subjected to heating, and in particular with betadicarbonyl compounds of formula (II):

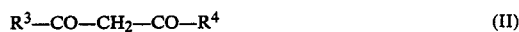

in which $R^3$ and $R^4$ have the meanings defined in the text, in masses containing organic calcium and zinc salts as basic stabilizers.

7 Claims, No Drawings

POLY 1,4-DIHYDRO-2,6-DIMETHYLPYRIDINE-3,5-DICARBOXYLESTERS USEFUL AS THERMAL STABILIZERS FOR SYNTHETIC POLYMERS

This invention relates to poly 1,4-dihydro-2,6-dimethylpyridine-3,5-dicarboxylesters of general formula (I)

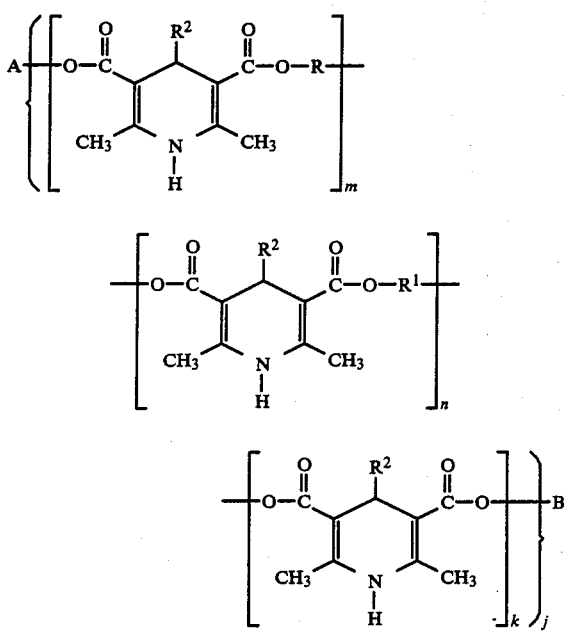

in which

A represents a linear or branched alkyl of 1-22 C atoms, possibly substituted with one or more groups chosen from alkoxy, alkylthio, hydroxyl possibly esterified with acrylic or methacrylic acid, halogen, aryl; phenyl or aryl of carbocyclic or heterocyclic type possibly substituted with one or more alkyl, alkoxy or halogen groups; alkenyl of 3-10 C atoms; $CH_3COCH_2$—COO—R—; $CH_3COCH_2COO$—$R^1$; $CH_3$—$C(NH_2)$=CH—COOR—; $CH_3$—$C(NH_2)$=CH—COO—$R^1$—; in which the amino group can carry one or more substituents of alkyl, hydroxyalkyl or alkoxyalkyl type or a cyclic substituent of polyalkylene or oxapolyalkylene type, or methylene or a linear or branched alkenyl of 2-22 C atoms;

B can assume the same meaning as A, or can represent a trivalent or polyvalent residue consisting of a linear or branched carbon atom chain possibly carrying substitutions of alkoxy, thioalkoxy, aryl, carboxyl or hydroxyl type;

m, n are whole numbers from 0 to 20, the sum of which is other than 0;

k can be 0 or 1;

j is a whole number from 1 to 6;

(k+m+n) is a whole number greater than 1;

R and $R^1$ each independently represent a bivalent hydrocarbon residue, a methylene or phenylene group, or a bivalent residue comprising at least one alkylene group of the type:

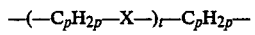

in which p is a whole number from 2 to 18, t is a whole number from 0 to 10 and X can be oxygen or sulphur, said alkylene group possibly carrying substitutions of alkoxy or thioalkoxy, aryl, carboxyl or hydroxyl type; or R and $R^1$ represent a direct bond with B only if k is 0 and j is greater than 1:

$R^2$ represents hydrogen or a monovalent residue of linear or branched alkyl, alkoxycarbonyl or aryl type possibly substituted with one or more alkyl, alkoxy, halogen or $NO_2$ groups.

The sequence of units which are repeated m and n times (for m+n greater than or equal to 3) can be of alternating type (a), block type (b) or random type (c).

The compounds of general formula (I) are useful as thermal stabilizers for synthetic polymers, in particular for polyvinylchloride-based masses.

For the correct conversion of PVC-based masses by thermal processes and the subsequent preservation of the manufactured articles under photooxidative conditions, it is necessary to add to said masses primary thermostabilizers and photostabilizers which are mostly based on organic metal derivatives (Chevassus et al., The Stabilization of Polyvinylchloride, 1963). This practice has lead to the identification of precise combinations of said organic metal derivatives with other organic substances such as alkyl, aryl or arylalkyl phosphites, epoxy or phenol derivatives, possessing high stabilizing efficiency.

In these mixtures each component performs a specific role by means of curative action, ie action directed towards repairing any damage produced in the polymer matrix (modification by interruption of the conjugation in the polyene chain, or modification of its ionic state), or preventive action, ie action directed towards preventing possible molecular damage (hydrochloric acid capture, interruption of the chain dehydrohalogenation, primary radical capture or hydroperoxide decomposition, etc.) in the chain degradation process which is triggered by thermal or photochemical effect (R. Gaechter, H. Mueller, Taschenbuch der Kunststoff-Additive, C. Hanser Verlag, 2 Ausgabe, 1983).

Lead, cadmium and tin-based compounds have for many years been the mainstays of this stabilization technique, and in part continue to be so. Given the general tendency towards the elimination of possible sources of toxicity in the environment, and because of the widespread distribution of PVC articles (10 million tons sold worldwide in 1980) the resources directed towards the use of primary stabilizer combinations which are progressively safer from the environmental toxicological viewpoint have been enormous. Although barium-zinc combinations have largely replaced barium-cadmium combinations, the modern tendency is towards calcium-zinc combinations which are so toxicologically safe as to be accepted by nearly all the legislation of industrialised countries, even in the case of articles intended for contact with food.

Unfortunately, calcium and zinc derivatives do not possess high thermal stabilization efficiency and require the co-use of specific compounds which not only give improved thermal stability but in addition do not prejudice photochemical stability. Thus use is now made of Ca/Zn carboxylate—epoxidised soya oil—organotin mercaptide and maleate combinations.

Perfecting these associations for industrial purposes has nevertheless required the co-use of organic co-stabilizers possessing high efficiency and low toxicity.

Compounds which have been studied and developed include alphaphenylindole (DE-PS No. 862512—1942—Bayer AG), diphenylthiourea (DE-PS No. 746081—1940—I. G. Farben Ind. A. G.), betaaminocrotonates [A. Michel, T. V. Hoang, A. Guyot, J. Macromol. Sci. Chem. A 12,411 (1978)], lactones containing carbonyl groups such as dehydroacetic acid (Belg. Pat. No. 875940—1979—S. A. Argus) and more recently betadiketone derivatives such as dibenzoylmethane and stearoylbenzoylmethane (Fr. 2297227 and Fr. No. 2324681—1975—Rhone Poulenc and JK No. 76, 111252—1975—Akishima).

1,4-dihydro-2,6-dimethylpyridine-3,5-dicarboxylesters, originally proposed in 1973 as thermal stabilizers for PVC (FR No. 2239496—1973—Societé Chimique des Charbonnages), have been more recently developed as thermal and photochemical stabilizers for PVC (FR No. 2405974, 2429806, 2433034—11977—LABAZ), including in synergic combinations with 2-phenylindole derivatives (FR No. 2407236, 2439215—1977—LABAZ), with organotin compounds (FR No. 79/25414—1979—Omnium Financier Aquitaine pour l'Hygiene et la Sante), with betaaminocrotonates (FR No. 2491480—1980—SANOFI), with betadiketones (FR No. 2534263—1982, EP No. 5678—1978, Rhone Poulenc; EP No. 51334—1981, Solvay), with phenoli and sulphurated antioxidants (EP No. 24754—1797—Solvay), with zinc mercaptoester salts (U.S. application Ser. No. 269085—1981—CARSTAB) and with various organometallic compounds (EP No. 2007—1979—CIBA GEIGY).

However, some of these compounds have intrinsic drawbacks. For example when incorporated in PVC articles, betaaminocrotonates release ammonia with time or during thermal processing. Some dihydropyridines and alphaphenylindole easily sublime under PVC working conditions; some compounds such as dehydroacetic acid are unstable under heat and acidity; alphaphenylindole has poor light stability; other compounds are difficult to prepare; still others easily migrate or are extracted by the solutions which come into contact with articles prepared from them when used as wrapping for example for food.

It has now been surprisingly found that many of the aforesaid drawbacks do not occur, and that improved thermal stabilization of PVC-based masses containing primary stabilizers is obtained if the compounds according to the present invention are used in them, these being new compounds and being characterised by the molecular structure of formula (I) as defined heretofore.

Preferred compounds of formula (I) are those in which:

A, B, which can be the same or different, each independently represent a linear or branched $C_1$-$C_{18}$ alkyl group;

m, k, j=1;

n=0;

R represents a —$(CH_2)_2$—, —$(CH_2)_4$— or —$(CH_2)_2$—S—$(CH_2)_2$— group;

$R^2$ represents hydrogen.

Examples of compounds represented by formula (I) are oligomers, polymers or in any event molecules of high molecular weight, characterised by containing two or more nuclei of 1,4-dihydro-2,6-dimethylpyridine-3,5-dicarboxylic acid (DHPC) variously esterified with monofunctional, difunctional or polyfunctional alcohols.

If the compounds of formula (I) are linear oligomers or polymers, A and B can represent residues of monovalent alcohols such as methyl, ethyl or dodecyl, whereas R and $R^1$ represent residues of bivalent alcohols such as ethylene or butylene glycol, thiodiglycol etc; in the case of polymers or oligomers deriving from different monomer units (R different from $R^1$) the sequence can be random, alternating or of block type.

When the compounds of formula (I) are branched polydihydropyridines, the heterocyclic units are not all connected in linear sequence and then for example A represents a residue of a monovalent alcohol such as methanol, ethanol etc., B represents a residue of a tri or polyvalent alcohol such as glycerin, trimethylol propane, pentaerythritol, sorbitol etc., and R and $R^1$ have the same meaning as for linear polymers.

$R^2$ is preferably a linear or branched alkyl of methyl or isopropyl type, a phenyl or an alkoxycarbonyl.

Table 1 shows some combinations of chemical groupings which when inserted into formula (I) form structures which represent and exemplify the compounds according to the present invention.

TABLE 1

| SYMBOL | No. | A | B | R |
|---|---|---|---|---|
| BGE | 1 | $C_2H_5$ | A | —$(CH_2)_4$— |
|  | 2 | $CH_2$=CH—COO$(CH_2)_4$— | A | —$(CH_2)_4$— |
| TGD | 3 | $C_{12}H_{25}$ | A | —$(CH_2)_2$—S—$(CH_2)_2$— |
|  | 4 | $CH_3$ | A | —$(CH_2)_4$— |
| BG3D | 5 | $C_{12}H_{25}$ | A | —$(CH_2)_4$— |
| T2B1E | 6 | $C_2H_5$ | A | —$(CH_2)_2$—S—$(CH_2)_2$— |
|  | 7 | $C_{12}H_{25}$ | A | —$(CH_2)_4$— |
|  | 8 | $CH_3$ | A | —$(CH_2)_4$— |
|  | 9 | $C_6H_5$ | A | —$(CH_2)_4$— |
| BGnAA | 10 | $CH_3COCH_2COO(CH_2)_4$— | A | —$(CH_2)_4$— |
|  | 11 | $CH_3C(NH_2)$=CHCOO$(CH_2)_4$— | A | —$(CH_2)_2$—S—$(CH_2)_2$— |
|  | 12 | $C_2H_5$ | $C_2H_5$—C= | —$CH_2$— |
|  | 13 | $C_2H_5$ | C= | —$CH_2$— |
|  | 14 | $CH_3$ | C= | —$(CH_2)_4$— |
|  | 15 | $CH_3$ | A | —$(CH_2)_4$— |
|  | 16 | $CH_3$ | A | —$(CH_2)_2$—S—$(CH_2)_2$— |
| TGnAC | 17 | $CH_3C(NH_2)$=CHCOO—$(CH_2)_2$—S—$(CH_2)_2$— | A | —$(CH_2)_2$—S—$(CH_2)_2$— |
| BGD | 18 | $C_{12}H_{25}$ | A | —$(CH_2)_4$— |
| BG3E | 19 | $C_2H_5$ | A | —$(CH_2)_4$— |
| BG7E | 20 | $C_2H_5$ | A | —$(CH_2)_4$— |
| BGM | 21 | $CH_3$ | A | —$(CH_2)_4$— |
| TGE | 22 | $C_2H_5$ | A | —$(CH_2)_2$—S—$(CH_2)_2$— |
| TGM | 23 | $CH_3$ | A | —$(CH_2)_2$—S—$(CH_2)_2$— |
| T4B3E | 24 | $C_2H_5$ | A | —$(CH_2)_2$—S—$(CH_2)_2$— |

TABLE 1-continued

| Symbol | No. | R¹ | R² | m | n | k | j | sequence |
|---|---|---|---|---|---|---|---|---|
| BGE | 1 | — | H | 1 | 0 | 1 | 1 | — |
|  | 2 | — | H | 1 | 0 | 1 | 1 | — |
| TGD | 3 | — | H | 1 | 0 | 1 | 1 | — |
|  | 4 | —(CH$_2$)$_2$—S—(CH$_2$)$_2$— | H | 1 | 1 | 1 | 1 | — |
| BG3D | 5 | — | H | 3 | — | 1 | 1 | — |
| T2B1E | 6 | —(CH$_2$)$_4$— | H | 2 | 1 | 1 | 1 | a |
|  | 7 | —(CH$_2$)$_2$—S—(CH$_2$)$_2$— | H | 3 | 2 | 1 | 1 | a |
|  | 8 | —(CH$_2$)$_2$—S—(CH$_2$)$_2$— | H | 3 | 4 | 1 | 1 | b |
|  | 9 | —(CH$_2$)$_2$—O—(CH$_2$)$_2$— | H | 12 | 6 | 1 | 1 | c |
| BGnAA | 10 | — | H | 15 | — | 1 | 1 | — |
|  | 11 | —(CH$_2$)$_4$— | H | 4 | 4 | 1 | 1 | a |
|  | 12 | — | H | 3 | 0 | 0 | 1 | — |
|  | 13 | — | H | 4 | 0 | 0 | 1 | — |
|  | 14 | —CH$_2$— | H | 1 | 1 | 0 | 1 | — |
|  | 15 | — | CH$_3$ | 1 | 0 | 1 | 1 | — |
|  | 16 | — | C$_6$H$_5$ | 1 | 0 | 1 | 1 | — |
| TGnAC | 17 | — | H | 15 | — | 1 | 1 | — |
| BGD | 18 | — | H | 1 | 0 | 1 | 1 | — |
| BG3E | 19 | — | H | 3 | 0 | 1 | 1 | — |
| BG7E | 20 | — | H | 7 | 0 | 1 | 1 | — |
| BGM | 21 | — | H | 1 | 0 | 1 | 1 | — |
| TGE | 22 | — | H | 1 | 0 | 1 | 1 | — |
| TGM | 23 | — | H | 1 | 0 | 1 | 1 | — |
| T4B3E | 24 | —(CH$_2$)$_4$— | H | 4 | 3 | 1 | 1 | — |

It has also been surprisingly found that in PVC-based masses containing primary stabilizers the combined use of compounds of formula (I) together with betadiketone compounds of formula (II) or together with metallic or organotin salts of enolates of compounds of formula (II):

$$R^3—CO—CH_2—CO—R^4 \quad (II)$$

in which:

R³ represents linear or branched C₁-C₁₈ alkyl, or an aromatic phenyl ring possibly substituted with one or more alkyl, alkoxy or halogen groups;

R⁴ has the same meaning as R³, independently of R³, or represents a covalent bond, C₁-C₁₈ alkylene, polyvalent C₁-C₁₈ hydrocarbon, or —(C$_p$H$_{2p}$—X)$_t$—C$_p$H$_{2p}$— in which p, t, X have the meanings already given for formula (I), and directly linked to another —CO—CH$_2$—CO—R³ group, results in thermal stabilization of synergic type exceeding the sum of that of the individual components, namely compounds (I) and compounds (II).

Compounds of formula (II) are known in the PVC stabilization field; examples are benzoylstearoylmethane, dibenzoylmethane (FR No. 2297227 and Fr 2324681), 1,12-dibenzoyldodecane-2,11-dione and 1,4-dibenzoylbutane-2,3-dione (EP No. 14508 and EP No. 46161).

Compounds of formula (I) according to the present invention are obtained by suitable use of the Hantzsch synthesis in one of the three most known variations [U. Eisner, J. Kuthan, Chem. Rev. 72 (1), 1–42 (1972); F. Bossert, H. Meyer, E. Wehiger, Angew. Chem. Int. Ed. Eng., 20, 762–765 (1981)], as follows:

(A) Condensation of an aldehyde with a bisacetoacetate and ammonia with water elimination [the corresponding esters of betaaminocrotonic acid of formula (IV) are obtained as intermediates]

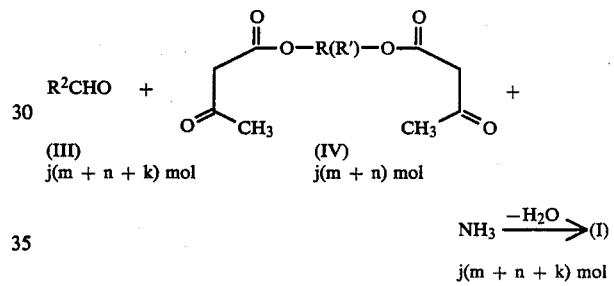

By using mixtures of acetoacetates (IV) (R different from R¹), compounds of mixed composition and random sequence are obtained.

The molecular weight and thus the length of the linear oligomer or polymer chain can be regulated by introducing an adequate predetermined quantity of monofunctional acetoacetates (V) or betaaminocrotonates (VII) which act as chain terminators;

$$CH_3—CO—CH_2—COO—X \quad (V)$$

$$H_2N—\underset{\underset{CH_3}{|}}{C}=CH—COO—X \quad (VII)$$

in which in the monofunctional compound X=CH₃, C₂H₅ or C₁₂H₂₅; in the tri or polyfunctional compound X=C(CH$_2$—)$_4$ or CH$_3$—CH$_2$—C(CH$_2$—)$_3$.

If non-linear oligomers are to be obtained, the terminators used must be monofunctional acetoacetates (V), (j moles) together with tri or polyfunctional acetoacetates (containing j functions) (1 mole), such as pentaerythrityl tetrakisacetoacetate.

The ammonia can be introduced in the form of gas or is preferably generated in situ from labile compounds such as ammonium carbonate or ammonium acetate, or from hexamethylenetetramine if the aldehyde is formaldehyde.

(B) Condensation of an aldehyde with a bis-betaaminocrotonate and elimination of water and ammonia;

In the particular case of dimer compounds, the following synthesis schemes are used:

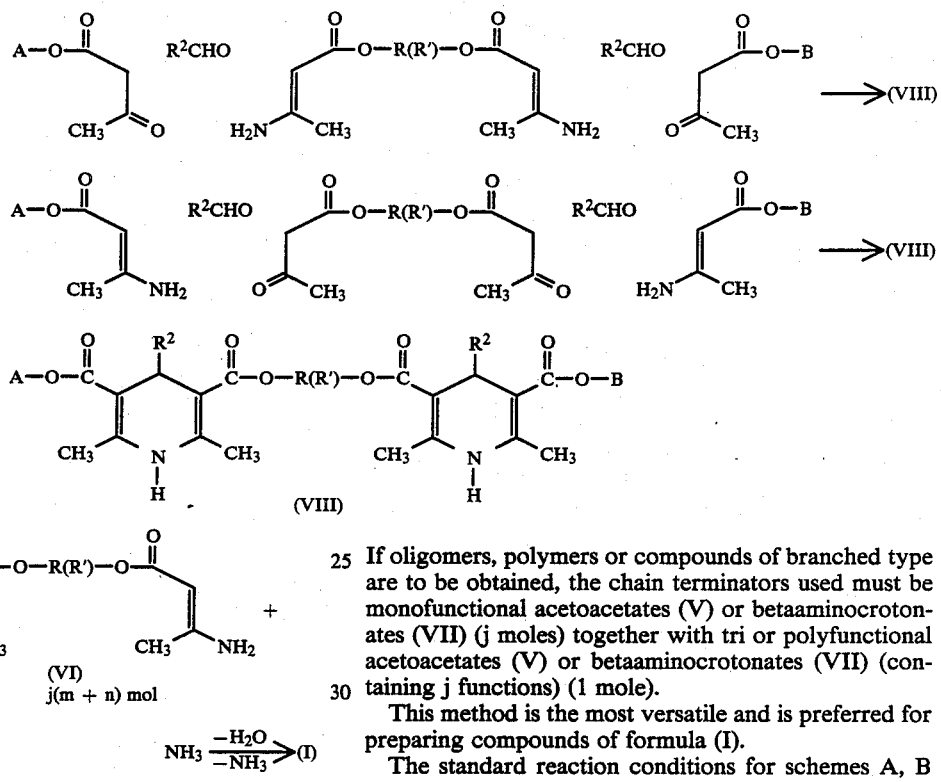

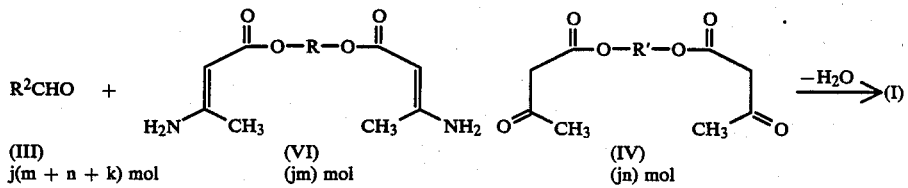

By using mixtures of betaaminocrotonates (VI) (R different from R¹), mixed compounds of random sequence are obtained. The molecular weight and thus the length of the linear oligomer or polymer chain can be regulated by introducing an adequate predetermined quantity of monofunctional betaaminocrotonates (VII) or acetoacetate (V) to act as chain terminators.

If non-linear oligomers are required, the chain terminators used must be betaaminocrotonates (VII) (j moles) together with betaaminocrotonates of tri or polyfunctional type (containing j amino groups) (1 mole) such as trimethylolpropane trisbetaaminocrotonate.

(C) Condensation of an aldehyde with a bis-betaaminocrotonate and a bis-acetoacetate and elimination of water;

By using the synthetic scheme in sequential controlled manner, ie implementing the condensation in consecutive stages with different ratio pairs of acetoacetates and betaaminocrotonates, it is possible to obtain oligomers or polymers of alternating sequence or block type in accordance with a predetermined structure. The molecular weight and thus the oligomer or polymer chain length is regulated by introducing suitable predetermined quantities of monofunctional terminators of the aminocrotonate type (VII) or acetoacetate type (V).

If oligomers, polymers or compounds of branched type are to be obtained, the chain terminators used must be monofunctional acetoacetates (V) or betaaminocrotonates (VII) (j moles) together with tri or polyfunctional acetoacetates (V) or betaaminocrotonates (VII) (containing j functions) (1 mole).

This method is the most versatile and is preferred for preparing compounds of formula (I).

The standard reaction conditions for schemes A, B and C comprise the use of a low-boiling alcoholic solvent, preferably isopropyl alcohol, and a heating stage of 1-20 hours. During the reaction the reagents, initially not all soluble, pass into solution and on termination generally a crystalline precipitate forms. The solvent is then removed or the reaction mixture diluted with water. After separation by filtration, the reaction product can be purified by crystallisation or by repeated washing with a suitable solvent.

The compounds of formula (I) are generally crystalline solids of defined melting point, light yellow in colour and possessing fluorescence, they being poorly soluble in common organic solvents and practically insoluble in water.

The following examples illustrate the preparation of compounds of formula (I) and their chemico-physical characteristics. Parts and percentages are by weight.

EXAMPLE 1 (Synthesis from acetoacetates):

Poly [1,4-dihydro-2,6-dimethyl-3,5-dicarboxypyridine-monobutylene ester] (BGnAA, compound 10, Table 1)

51.65 g of dibutyleneglycolbisacetoacetate, 3.1 g of methylacetoacetate, 10.5 g of hexamethylenetetramine, 2.9 g of ammonium acetate and 60 ml of isopropylalcohol containing 20 g of water are placed in a 250 ml flask. The mixture is heated to 60° C. over 1 hour and kept at this temperature for 1 hour, after which it is heated under reflux for 3 hours and then left at rest overnight at 20° C. The suspension is poured into water under effective agitation. The yellow solid obtained is separated by filtration and washed repeatedly with water and then with acetone. After drying at 40° C. under vacuum, 42.7 g of product are obtained with a M.P. of 175° C.

EXAMPLE 2 (Synthesis from betaaminocrotonates)

Poly [1,4-dihydro-2,6-dimethyl-3,5-dicarboxypyridinemonothiodiglycolester] (TGnAC, compound 17, Table 1)

8.65 g of thioglycolbisaminocrotonate, 0.49 g of methylbetaaminocrotonate, 3.0 g of aqueous formaldehyde (38% by weight) and 50 ml of isopropylalcohol are placed in a 250 ml flask. The mixture is heated to 60° C. over 1 hour and then under reflux for 6 hours, after which it is left at rest overnight at 20° C. The suspension is poured into water under effective agitation. The yellow solid obtained is separated by filtration, washed repeatedly with water and then with acetone. After drying at 40° C. under vacuum, 7.38 g of product are obtained with a M.P. of 156° C.

EXAMPLE 3 (Mixed synthesis)

(TGD, compound 3, Table 1)

150 ml of isopropyalcohol, 14.6 g of thiodiglycolbisaminocrotonate, 28.2 g of dodecylacetoacetate and 3 g of paraformaldehyde are placed in a 250 ml flask. The mixture is agitated under nitrogen for 10 minutes and then heated under reflux for 40 minutes. 80 ml of water are added and heating continued at 80° C. for 30 minutes. The mixture is cooled to 20° C., the yellow solid obtained is filtered off and washed with water and then with 80 ml of acetone. It is dried under vacuum at 40° C. to obtain 32.5 g of product of M.P. 146° C.

EXAMPLE 4 (Mixed synthesis)

(BG3D, compound 5, Table 1)

100 ml of isopropylalcohol, 25.6 g of butyleneglycolbisaminocrotonate, 12.9 g of butyleneglycolbisacetoacetate and 6 g of paraformaldehyde are placed in a 250 ml flask at 20° C. The mixture is agitated at 20° C. for 10 minutes and then at 80° C. for 120 minutes. 27.04 g of dodecylacetoacetate dissolved in 30 ml of isopropylalcohol are then fed in over 10 minutes.

The mixture is kept at 80° C. for 1 hour after which 80 ml of water are added.

After 30 minutes the mixture is cooled to 20° C. and the solid which forms is filtered off, washed with water and then with 50 ml of acetone. It is dried under vacuum at 40° C. to obtain 54 g of product of M.P. 168° C.

Other compounds were obtained in an analogous manner, their chemico-physical and chemical characteristics being shown in Tables 2 and 3.

Spectroscopic characteristics (infrared, ultraviolet and NMR spectra), elementary analysis, thin layer chromatographic data and the synthesis procedure confirm the structure of the products obtained.

TABLE 2

| | (General physico-chemical characteristics) | | | |
|---|---|---|---|---|
| Comp. symbol | BGM | BGE | BG3E | BG7E |
| No. (Tab. 1) | 21 | 1 | 19 | 20 |
| APPEARANCE | fluorescent light yellow powder | | | |
| MELTING POINT °C. | 183 | 168 | 173 | 154 |
| INFRARED SPECTRUM | 3355 | 3360 | 3355 | 3355 |
| (Absorption, cm$^{-1}$) | 1700 | 1700 | 1700 | 1700 |
| | 1660 | 1650 | 1660 | 1650 |
| | 1510 | 1510 | 1510 | 1505 |
| | 1305 | 1305 | 1305 | 1220 |
| | 1220 | 1220 | 1220 | 1105 |
| | 1115 | 1120 | 1115 | 750 |
| | 750 | 745 | 750 | |
| TLC (silica, eluent chloroform 4, acetone 1) (R$_7$) | 0.50 | 0.47 | 0.02 | 0.01 |
| SOLUBILITY (g/l) | | | | |
| Water | insoluble | insoluble | insoluble | insoluble |
| Gl. acetic acid | <0.25 | | | |
| 95% ethanol | <0.3 | <0.3 | | |
| Chloroform | 0.5 | | | |
| Acetone | 0.6 | | | |
| Dioctylphthalate | <0.2 | | | |
| VOLATILITY % weight loss at 210° C. for 10 minutes | 6 | | | |
| EMPIRICAL FORMULA | $C_{24}H_{32}ON_2O_9$ | $C_{26}H_{36}N_2O_9$ | $C_{52}H_{70}N_4O_{16}$ | $C_{104}H_{139}N_9O_{32}$ |
| MOLECULAR WEIGHT | 476.35 | 504.57 | 1007.14 | 2012.3 |

| | (General physico-chemical characteristics) | | | | |
|---|---|---|---|---|---|
| Comp. symbol | TGE | TGD | T2B1E | T4B3E | TGnAC |
| No. (Tab. 1) | 22 | 3 | 6 | 24 | 17 |
| APPEARANCE | fluorescent light yellow powder | | | | |
| MELTING POINT °C. | 146 | 146 | 125 | 127 | 156 |
| INFRARED SPECTRUM | 3350 | 3345 | 3350 | 3350 | 3350 |
| (Absorption, cm$^{-1}$) | 1700 | 1700 | 1700 | 1700 | 1700 |
| | 1650 | 1660 | 1660 | 1660 | 1660 |
| | 1500 | 1500 | 1500 | 1500 | 1500 |
| | 1385 | 1296 | 1385 | 1385 | 1300 |
| | 1300 | 1220 | 1220 | 1210 | 1210 |
| | 1220 | 1120 | 1110 | 1110 | 1110 |
| | 1110 | 1100 | 1100 | 1010 | 1100 |
| | 1100 | 965 | 756 | 760 | 1005 |

TABLE 2-continued

|  | 1010 750 | 750 |  |  | 750 |
| --- | --- | --- | --- | --- | --- |
| TLC (silica, eluent chloroform 4, acetone 1) ($R_7$) | 0.46 | 0.67 | 0 | 0 | 0 |
| SOLUBILITY (g/l) |  |  |  |  |  |
| Water | insoluble | insoluble | insoluble | insoluble | insoluble |
| Gl. acetic acid |  | <0.2 |  |  |  |
| 95% ethanol |  | <0.2 |  |  |  |
| Chloroform |  | 20 |  |  |  |
| Acetone |  | <0.15 |  |  |  |
| Dioctylphthalate |  | <0.1 |  |  |  |
| VOLATILITY % weight loss at 210° C. for 10 minutes |  | 1.3 |  |  | 1.5 |
| EMPIRICAL FORMULA | $C_{26}H_{36}N_2O_8S$ | $C_{46}H_{76}N_2O_8S$ | $C_{52}H_{70}N_4O_{16}S$ | $C_{104}H_{138}N_8O_{32}S_4$ | $C_{206}H_{270}N_{16}O_{64}S_{15}$ |
| MOLECULAR WEIGHT | 536.64 | 817.16 | 1071.26 | 2140.54 | 4474.37 |

(General physico-chemical characteristics)

| Comp. symbol | BGD | BG3D | BGnAA | TGM |
| --- | --- | --- | --- | --- |
| No. (Tab. 1) | 18 | 5 | 10 | 23 |
| APPEARANCE | fluorescent light yellow powder | | | |
| MELTING POINT °C. | 165 | 168 | 175 | 157 |
| INFRARED SPECTRUM (Absorption, cm$^{-1}$) | 3360 1700 1660 1510 1220 750 | 3350 1695 1650 1505 1305 1220 750 | 3350 1695 1660 1505 1303 1220 750 | 3350 1697 1660 1505 1302 1225 1120 750 |
| TLC (silica, eluent chloroform 4, acetone 1) ($R_7$) | 0.69 | 0.05 | 0 | 0.42 |
| SOLUBILITY (g/l) |  |  |  |  |
| Water | insoluble | insoluble | insoluble | insoluble |
| Gl. acetic acid | <0.2 |  | <0.2 | <0.2 |
| 95% ethanol | <0.2 |  |  | <0.2 |
| Chloroform | 1.6 |  |  | 6.7 |
| Acetone | 1.2 |  | 0.5 | <0.35 |
| Dioctylphenalate | <0.13 |  |  | <0.1 |
| VOLATILITY % weight loss at 210° C. for 10 minutes | 2.01 |  | 1.6 | 7.8 |
| EMPIRICAL FORMULA | $C_{46}H_{76}N_2O_9$ | $C_{72}H_{110}N_4O_{16}$ | $C_{206}H_{270}N_{16}O_{64}$ | $C_{24}H_{32}N_2O_9S$ |
| MOLECULAR WEIGHT | 785.10 | 1287.68 | 3393.38 | 508.58 |

CHARACTERISATION EXAMPLES

BGD (compound 18)

| NMR spectrum (CDCl$_3$): | δ (ppm) | 0.86 | 1.25 | 1.60 | 1.76 | 2.18 | 3.28 | 4.09 | 5.15 |
| --- | --- | --- | --- | --- | --- | --- | --- | --- | --- |
|  | multipl. | t | s | q | m | s | s | t | s |
|  | No. H | 6 | 36 | 4 | 4 | 12 | 4 | 8 | 2 |
| UV spectrum (CHCl$_3$): | λmax = 242 nm, | | | | $\epsilon_{242}$ = 17230 (M$^{-1}$cm$^{-1}$) | | | | |
|  | λmax = 360 nm, | | | | $\epsilon_{360}$ = 12178 (M$^{-1}$cm$^{-1}$) | | | | |
| Elementary analysis: | | C | | | H | | | N | |
| calculated | | 70.37 | | | 9.75 | | | 3.57 | |
| found | | 69.60 | | | 9.82 | | | 3.38 | |

TGM (compound 23)

| NMR spectrum (P$_y$D$_5$): | δ (ppm) | 2.48 | 3.09 | 3.81/3.82 | 4.6 | 9.5 |
| --- | --- | --- | --- | --- | --- | --- |
|  | multipl. |  | 2s | t | 2s | t | s (broad) |
|  | No. H |  | 12 | 4 | 6 + 4 | 4 | 2 |
| UV spectrum (CHCl$_3$): | λmax = 244 nm, | | | $\epsilon_{244}$ = 16419 (M$^{-1}$cm$^{-1}$) | | |
|  | λmax = 364 nm, | | | $\epsilon_{364}$ = 11411 (M$^{-1}$cm$^{-1}$) | | |
| Elementary analysis: | | C | | H | | N |
| calculated | | 56.58 | | 6.33 | | 5.50 |
| found | | 55.82 | | 6.28 | | 5.27 |

BGnAA (compound 10)

| NMR spectrum (P$_y$D$_5$): | δ (ppm) | 1.92 | 2.48 | 3.87 | 4.4 | 9.0 |
| --- | --- | --- | --- | --- | --- | --- |
|  | multipl. | m | s | s | m | s (broad) |
|  | No. H | 4 | 6 | 2 | 4 | 1 |
| UV spectrum (CHCl$_3$): | λmax = 242 nm, | | | $\epsilon_{242}$ = 74875 (M$^{-1}$cm$^{-1}$) | | |
|  | λmax = 367 nm, | | | $\epsilon_{367}$ = 37440 (M$^{-1}$cm$^{-1}$) | | |
| Elementary analysis: | | C | | H | | N |
| calculated | | 61.95 | | 6.81 | | 5.6 |
| found | | 61.17 | | 6.89 | | 4.49 |

TGD (compound 3)

TABLE 2-continued

| NMR spectrum (CDCl$_3$): | δ (ppm) | 0.85 | 1.25 | 1.62 | 2.17/2.18 | 2.85 | 3.25 | 4.08 | 4.15 | 5.2 |
|---|---|---|---|---|---|---|---|---|---|---|
| | multipl. | t | s | q | 2s | t | s | t | t | s |
| | No. H | 6 | 36 | 4 | 12 | 4 | 4 | 4 | 4 | 2 |
| UV spectrum (CHCl$_3$): | | λmax = 245 nm, | | | | $\epsilon_{245}$ = 16397 (M$^{-1}$cm$^{-1}$) | | | | |
| | | λmax = 365 nm, | | | | $\epsilon_{365}$ = 12738 (M$^{-1}$cm$^{-1}$) | | | | |
| Elementary analysis: | | | C | | | | H | | N | |
| calculated | | | 67.09 | | | | 9.37 | | 3.42 | |
| found | | | 66.78 | | | | 9.43 | | 3.33 | |

The compounds of formula (I) according to the present invention are advantageously used in the thermal stabilization of synthetic polymers, particularly of masses based on PVC (obtained by polymerisation undiluted, in suspension or in emulsion), on various copolymers such as vinyl chloride/vinyl esters and on vinyl chloride/vinylidene chloride copolymers.

It has been surprisingly found that the use of said compounds in said masses in association with common primary Ca/Zn or Mg/Zn stabilizers, such as Ca/Zn stearates, when used mainly in association with epoxidised soya oil and organic mono or dioctyltin salts, in formulations suitable for the production of either rigid or flexible articles, results in high-efficiency thermal stabilization.

In particular, in a stabilizing mixture consisting of Ca/Zn stearates, epoxidised soya oil and dioctyltin bisisooctylthioglycolate, it is possible to partly or totally replace the tin derivative with a much smaller quantity of compounds of formula (I) either alone or in combination with compounds of formula (II) to obtain equal thermal stabilization efficiency.

The compounds of formula (I) either alone or in combination with compounds of formula (II) can also be used in PVC masses in association with primary stabilizers of Ba/Zn or Ba/Cd type. For example in the form of their maleic, 2-ethylhexanoic or 4-tert-butylbenzoic acid salts, commonly used together with organic phosphites such as tris-nonylphenylphosphite, decyldiphenylphosphite, tridecylphosphite etc., or can be used in association with stabilizers based on organic or inorganic lead derivatives, with advantages analogous to those stated heretofore.

The quantity of compounds of formula (I) to be used varies from 0.01 to 3% by weight of the polymer to be stabilized, and preferably between 0.1 and 0.5%.

It has also been surprisingly found that if, in masses containing primary stabilizers, compounds of formula (I) are used together with organic stabilizers such as betadicarbonyl compounds, a synergic stabilization effect is obtained, ie exceeding the sum of the effects of the compounds of formula (I) and the said stabilizers of formula (II) taken individually. Particularly preferred is the synergic combination with betadiketone compounds of formula (II) such as benzoylstearoylmethane, dibenzoylmethane, 1,4-dibenzoylbutane-2,3-dione, benzoylacetone, 1,12-dibenzoyldodecane-2,11-dione or metal or organotin salts of the respective enolates. The ratio of compounds of formula (I) to betadicarbonyl compounds of formula (II) can lie between 1:10 and 10:1, and preferably between 1:2 and 4:1.

A further aspect of using compounds of formula (I) derives from the fact that the masses obtained have excellent stability under photooxidative conditions when subjected to the action of light under natural conditions by exposure to solar light or to radiation of lamps of various kinds.

The stability is much better than in the case of masses stabilized with 2-phenylindole derivatives or betadiketones.

The stabilizers of formula (I) can be incorporated either alone or together with compounds of formula (II) into PVC-based masses by simply mixing the compounds together with all the required ingredients, using a slow mixer, turbo mixer, Banbury mixer, extruder or double-roller mixer to obtain maximum uniformity before thermal transformation to produce the finished article.

The stabilized masses containing compounds of formula (I) either alone or together with compounds of formula (II) can be used for transformation operations comprising a thermal cycle, such as calendering, extrusion, injection-moulding, blow-moulding, thermoforming, spreading or rotary moulding, to obtain rigid or flexible articles, or expanded articles if suitable expanding agents are used.

The preferred uses of stabilized masses containing compounds of formula (I) possibly together with compounds of formula (II) are the manufacture of bottles by blow-moulding (blow-extrusion), rigid packages for food (for example by calendering), packaging in general by calendering and extrusion (possibly followed by vacuum-forming), film for general use, moulded or extruded articles etc.

Depending on the type of final use of the stabilizised masses, other additives can also be incorporated such as lubricants, mineral fillers, dyes, pigments, plasticisers, impact-strength modifiers, expanding agents, antiblocking agents, primary and secondary antioxidants, light stabilizers of various types such as UV radiation absorbers, optical bleaches etc.

The advantages consequent on the use of compounds of formula (I) either alone or in combination with compounds of formula (II) in PVC-based masses are various, and positively influence the transformation technology and the use of the final articles, and can be summarised as follows:

very high thermal stability (time necessary for carbonisation at a determined working temperature, under static or dynamic conditions); very high thermal stability of colour and transparency (time for which the colour and transparency of the article remain within a predetermined standard at a given working temperature);

absence of influence on lubrication properties (ability to hot-work the mass without it adhering to the machine walls or undergoing plastic flow);

absence of deposits on the machine due to the absence of sublimation when compounds of formula (I) are used either alone or with high molecular-weight compounds of formula (II);

reduction in formulation costs because of the high stabilizing efficiency of compounds of formula (I) used either alone or together with compounds of formula (II)

(possibility of reducing the quantities of base stabilizers or additives normally used);

improvement in environmental safety during formulation and transformation, by allowing reduction in the quantity of compounds considered ecologically unsafe such as cadmium, lead or organotin derivatives, while maintaining equal stabilizing effect;

high resistance to degradation by light under photooxidative conditions, even at high ambient temperature (50°–70° C.) and in the presence of water;

migration extremely reduced or absent by virtue of the poor solubility of compounds of formula (I) in nearly all cold substances due to their high molecular weight, coupled with their affinity for PVC-based masses;

reduction in toxicity of manufactured articles.

The following non-limiting examples illustrate in detail the applicational properties of compounds of formula (I) as thermal stabilizers for PVC-based masses.

Parts are by weight, and percentages refer to 100 parts of vinyl resin (PHR).

FORMULATIONS

1. Mixes for rigid transparent articles.

|  | A | B | C | D |
|---|---|---|---|---|
| S-PVC (K58) (1) | 100 | 100 | 100 | 80 |
| PVA (2) | — | — | — | 20 |
| MBS (modifier) (3) | 8 | 6 | 6 | 8 |
| PMMA (working auxiliary) (4) | 1.5 | 1.5 | 1 | — |
| ESO (epoxidised soya oil) (5) | 2.5 | 2 | 2 | 2 |
| Cetylstearyl alcohol | 1 | 1 | 1.5 | 0.5 |
| Calcium stearate | 0.4 | 0.36 | 0.36 | 0.3 |
| Zinc stearate | 0.4 | 0.2 | variab. | 0.3 |
| Organic stabilizer |  | variable |  |  |

(1) Sicron 230 (Montedison)
(2) Polyvinylacetate, Vinnol H 1157 (Wacker)
(3) Polymethylmethacrylate/butadiene/styrene, Paraloid 357 (Rohm & Haas)
(4) Polymethylmethacrylate, Paraloid K175 (Rohm & Hass)
(5) Edenol D 81 (Henkel)

2. Mixes for rigid pigmented articles.

| S-PVC (K 58) | 100 |
|---|---|
| PMMA | 1.5 |
| Cetylstearyl alcohol | 1 |
| Calcium carbonate (1) | 2 |
| Calcium stearate | 1 |
| Zinc stearate | 1 |
| Organic stabilizer | variable |

(1) BL R 3 (Omya)

3. Mixes for plasticised articles

|  | A | B |
|---|---|---|
| S-PVC (K 65) (1) | 100 | — |
| S-PVC (K 58) | — | 100 |
| DOP (dioctylphthalate) | 30 | 30 |
| ESO (epoxidised soya oil) | 3.0 | — |
| Calcium stearate | 0.4 | — |
| Zinc stearate | 0.4 | — |
| Pentaerythritol | 0.3 | — |
| Barium nonylphenolate carbonate (2) | — | 0.6 |
| Zinc 2-ethylhexanoate | — | 0.18 |
| Decyldiphenylphosphite | — | 0.4 |
| Organic stabiliser |  | variable |

(1) Sicron 540 (Motedison)
(2) Lubrizol 2106 (Lubrizol)

TEST METHODS

1. Preparation of mixes

1A—For static thermostability:

The mixture of ingredients is gelled in a double-roller mixer at 175° C. for 2 minutes (friction ratio 1:1). The sheet of 0.6 mm thickness is cooled rapidly on a flat surface.

1B—For dynamic thermostability:

The mixture of ingredients is gelled directly in a two-roller mixer at the temperature chosen for the stability test (friction ratio 1:1.5) which is then carried out. The sheet thickness is 0.6 mm.

2. Dynamic stability test

The mixture prepared as under point 1B is immediately passed to the two-roller mixer at the established temperature (friction ratio 1:1.5). At regular time intervals, sheets samples are withdrawn and are rapidly cooled on a flat surface. The test continues until incipient carbonisation. The time required to attain this is known as the long-term stability time. The stability values at intermediate times are evaluated by comparing the colour of the respective sheet samples, measured by the yellowing index (YI) in accordance with ASTM D 1925-70 standard. The longer the long-term stability time and the lower the yellowing index, the more thermally stable the material.

3. Static stability test

The sheet pregelled as under point 1A is cut into 3×3 cm pieces, which can be treated thermally in a temperature-controlled oven from which they are extracted at regular time intervals.

Alternatively, ageing can be effected in a temperature-controlled press (3 Atm) for different times.

The sheets, contained between mirror surfaces, measure 0.6 mm in thickness.

The long-term and intermediate stabilities are evaluated using the same criteria as for dynamic stability.

Both in the case of static stability and in the case of dynamic stability the yellowing indices are measured until incipient carbonisation (the time associated with the latter then being long-term stability).

4. Lubrication test

Lubrication is evaluated by carrying out the test in the same manner as described for dynamic stability, but measuring the total time which passes before the mixture sticks to the rollers.

The longer the measured time the more lubricated the material.

5. Transparency test

The sheet prepared as under point 1A is inserted into a press (3 Atm) between polished surfaces to obtain strips of 0.6 mm thickness. The coefficient of reflection on a black background and on a white background are measured through the depth of the strips obtained. Transparency, defined as the contrast ratio, is given by the ratio of the coefficient of reflection against the black background to that against the white background (ASTM D The greater this ratio the poorer the transparency.

6. Plate out test

This test is carried out as for the dynamic stability test but interrupting mixing in the two-roller mixer before burning. The mixture used contains a red pigment.

Without cleaning the mixer rollers a white-pigmented (TiO$_2$/CaCO$_3$) mixture is then used for 2 minutes. The colour assumed by this second mixture is evaluated by arbitrary units (0 to 10). The greater the colour the greater the plate out.

The following examples relate to the application of compounds of formula (I) in the aforestated formulations.

EXAMPLE 5

Dynamic stability was evaluated at 180° C. on the formulation for rigid transparent articles (1A) using 0.3 PHR of organic stabilizer. The YI values are given.

|  | Time (minutes) | | | | |
| --- | --- | --- | --- | --- | --- |
|  | 5 | 10 | 15 | 20 | 25 |
| without stabilizer | 37.8 | 47.5 | 52.7 | 54.7 | 75.5 |
| FI (1) (a) | 23.9 | 28 | 30.9 | 33.8 | 39.2 |
| BGAC (2) (a) | 17.0 | 19.4 | 30.2 | 72.8 | sticks |
| TGAC (3) (a) | 18.1 | 19.8 | 29.6 | 66 | sticks |
| DHPL (4) (a) | 17.2 | 18.2 | 21.2 | 31.2 | 58.9 |
| SBBM (5) (a) | 10.2 | 15.6 | 29.8 | 52.6 | 93.7 |
| BGD | 16.5 | 17.9 | 20.3 | 27.7 | 58.8 |
| TGD | 16.8 | 17 | 19 | 26.2 | 58 |
| TGM | 15.8 | 15.8 | 16.8 | 22.9 | 58.5 |
| BG3D | 16 | 17.5 | 19.5 | 26.5 | 58.8 |
| BGnAA | 16.2 | 17.8 | 19.6 | 26.7 | 58.6 |

(1) 2-phenylindole
(2) butylglycol bisbetaaminocrotonate
(3) thiodiglycol bisbetaaminocrotonate
(4) 1,4-dihydro-2,6-dimethyl-3,5-dicarboxypyridinedidoecyl ester
(5) sebacoyl bisbenzoylmethane
(a) used as reference It will be noted that the compounds of the present invention are effective thermal stabilizers and substantially better than the compounds normally used. A comparison with betadiketones (SBBM) is also advantageous, these having an initially lighter colour but which decays rapidly to result in a worse long-term stability.

2-phenylindole has a better colour only a few minutes before burning.

The plate out was found low for all compounds (1-2).

EXAMPLE 6

Static stability was evaluated at 190° C. on the formulation for rigid pigmented articles (No. 2) using 0.3 PHR of organic stabilizer. The YI values are given.

|  | Time (minutes) | | | | |
| --- | --- | --- | --- | --- | --- |
|  | 1 | 2 | 3 | 4 | 5 |
| without stabilizer | 65.9 | 69 | 71.3 | 74.1 | 74.4 |
| DHPL (a) | 44.2 | 50 | 59.4 | 67.7 | 80 |
| BGD | 37.3 | 43.3 | 43.4 | 43.4 | 46.4 |
| TGD | 40.4 | 40.6 | 41.3 | 39.1 | 52.9 |
| TGM | 29.3 | 30.5 | 29.7 | 27.7 | 30.7 |

(a) used as reference

The compounds of the invention are excellent thermal stabilizers and are better than the structurally analogous one (a) normally used.

EXAMPLE 7

Dynamic stability was evaluated at 175° C. on a formulation for rigid transparent articles based on polyvinyl chloride-polyvinyl acetate copolymer in mixture with PVC (No. 1D) using 0.3 PHR of organic stabilizer. The YI values are given.

|  | Time (minutes) | | | |
| --- | --- | --- | --- | --- |
|  | 5 | 10 | 15 | 20 |
| without stabilizer | 24 | 31.1 | 50.2 | 87.7 |

-continued

|  | Time (minutes) | | | |
| --- | --- | --- | --- | --- |
|  | 5 | 10 | 15 | 20 |
| DHPL (a) | 10.9 | 12.7 | 35.6 | 85.1 |
| BGD | 9.8 | 11.9 | 24.3 | 77.2 |

(a) used as reference

The excellent thermal stability of the compounds of the invention can be seen, this being substantially better than that of currently used products.

EXAMPLE 8

Dynamic stability was evaluated at 180° C. on the formulation for plasticised articles (No. 3A) using 0.15 PHR of organic stabilizer. The YI values are given.

|  | Time (minutes) | | | | | |
| --- | --- | --- | --- | --- | --- | --- |
|  | 5 | 10 | 15 | 20 | 25 | 30 |
| without stabilizer | 10.5 | 14.4 | 18.7 | 19.8 | 17.7 | 28 |
| TGD | 9.1 | 8.4 | 7.7 | 8.2 | 10.1 | 17 |
| BGD | 8.5 | 7.9 | 7.6 | 8.1 | 11.4 | 16.5 |
| TGM | 10.5 | 9.3 | 8.2 | 8.0 | 9.7 | 16.1 |

Excellent thermal stability can be noted, with a particularly low colour until burning.

EXAMPLE 9

Dynamic stability was evaluated at 180° C. for BGD with different PHR values on a formulation for rigid transparent articles (No. 1B).

|  | Time (minutes) | | | | | | |
| --- | --- | --- | --- | --- | --- | --- | --- |
|  | 3 | 6 | 9 | 12 | 15 | 18 | 21 |
| without stab. | 40 | 54.2 | 62.2 | 71.3 | 80.1 | 97.1 | 111.8 |
| 0.05 PHR | 23.1 | 28.7 | 30.6 | 36 | 58.5 | 88.2 | 111.2 |
| 0.15 PHR | 20.7 | 23.6 | 24.4 | 25.7 | 47.5 | 84.7 | 116.2 |
| 0.30 PHR | 17.1 | 18.2 | 18.9 | 19.6 | 22.5 | 38.5 | 86.7 |
| 0.50 PHR | 16.2 | 17.1 | 18.3 | 15.5 | 24.5 | 40.2 | 94.4 |

An excellent stabilization efficiency can be noted over a wide percentage incorporation range of the compounds according to the invention. In particular, the efficiency is already high at very small incorporation quantities and tends to improve as the amount incorporated increases until it reaches an optimum value at 0.3 PHR (compare YI at 15 and 18 minutes).

EXAMPLE 10

Dynamic stability was evaluated at 180° C. on a formulation for rigid transparent articles (No. 1C) using 0.15 PHR of organic stabilizer (BGD) at different ratios of calcium to zinc stearate as primary stabilizer.

|  | Time (minutes) | | | | | | |
| --- | --- | --- | --- | --- | --- | --- | --- |
|  | 3 | 6 | 9 | 12 | 15 | 18 | 21 |
| Zinc stearate | | | | | | | |
| 0.1 PHR | 23.9 | 32 | 45.9 | 78 | 138.7 | — | — |
| 0.2 | 20.7 | 23.6 | 24.4 | 25.5 | 47.5 | 92.2 | 116.2 |
| 0.3 | 17.8 | 19.7 | 20.1 | 20.6 | 24.4 | 38.5 | 68.2 |

A sharp improvement in colour is noted together with a long-term thermal stability increase as the quantity of zinc stearate approaches that of calcium stearate (0.36 PHR).

EXAMPLE 11

Dynamic stability was evaluated at 180° C. on a formulation for plasticised articles (No. 3B, primary stabilizers Ba/Zn) using 0.3 PHR of organic stabilizer.

|  | Time (minutes) | | | | | | | | |
|---|---|---|---|---|---|---|---|---|---|
|  | 5 | 10 | 15 | 20 | 25 | 30 | 35 | 40 | 45 |
| without stab. | 19.2 | 27.6 | 31.2 | 30.6 | 26.9 | 24.5 | 21.7 | 21.9 | 61 |
| BGD | 16.1 | 22.3 | 24.1 | 23.7 | 21.4 | 21.1 | 19.1 | 23.9 | 69.5 |
| TGD | 16.1 | 21.6 | 24.0 | 23.0 | 20.6 | 19.1 | 18.6 | 53.5 | — |
| TGM | 15.7 | 21.7 | 22.6 | 21.3 | 19.3 | 18.1 | 17.3 | 23.4 | 68.2 |

The compounds of the invention contribute towards maintaining the colour of the stabilized masses within substantially narrower limits when subjected to temperature and mechanical stress. The plate out is very good and is low for all compounds (1–2).

EXAMPLE 12

The lubrication evaluation test was carried out at 190° C. on a mix for rigid transparent articles comprising S-PVC (K 58) 100 parts, MBS 6 parts, epoxidised soya oil 1 part, calcium stearate 0.2 parts and zinc stearate 0.1 part, using 0.5 PHR of organic stabilizer.

The time (in minutes) taken for the mix to stick to the mixer rollers when operating with a friction ratio of 1:1.25 is given.

| Organic stabilizer | — | TGD | BGD | TGM |
|---|---|---|---|---|
| Time | 21 min | 23 min | 22 min 30 sec | 22 min |

It can be noted that on using the compounds of the invention there are no negative effects on the mixture lubrication, and in fact the effects are slightly positive, the compounds with long-chain substituents (TGD and BGD) being slightly better than those with short-chain substituents (TGM).

EXAMPLE 13

The transparency test was carried out at 190° C. on a mix for rigid transparent articles (No. 1B) using 0.3 PHR of organic stabilizer. The contrast ratios are given.

| Stabilizer | — | TGD | BGD | TGM |
|---|---|---|---|---|
| Contrast ratio | 0.2707 | 0.2595 | 0.2604 | 0.2640 |

A substantial positive effect on the article transparency can be noted when using the compounds of the invention, this effect being slightly better for compounds with long-chain substituents.

The following examples relate to the application of compounds of formula (I) in association with compounds of formula (II).

EXAMPLE 14

Dynamic stability was evaluated at 180° C. on a formulation for rigid transparent articles (No. 1A) using the indicated quantities of organic stabilizer. The YI values are given.

|  | Stabilizer | | | Time (minutes) | | | | |
|---|---|---|---|---|---|---|---|---|
|  |  |  |  | 5 | 10 | 15 | 20 | 25 |
| 1 | TGD | 0.3 | PHR | 16.8 | 18 | 19 | 26.2 | 61 |
| 2 | SBBM | 0.3 | PHR (a) | 10.2 | 15.6 | 29.8 | 52.9 | 93.7 |
| 3 | TGD | 0.15 | PHR | 8 | 11.1 | 21.6 | 50 | 92 |
|  | SBBM | 0.15 | PHR |  |  |  |  |  |
| 4 | BSM | 0.3 | PHR (b) | 9.8 | 14.2 | 23.6 | 43.2 | 79 |
| 5 | TGD | 0.15 | PHR | 8.8 | 11.3 | 18.4 | 36.3 | 71.2 |
|  | BSM | 0.15 | PHR |  |  |  |  |  |
| 6 | TGD | 0.15 | PHR | 9.7 | 11.5 | 17.9 | 40.6 | 92 |
|  | SBBM | 0.15 | PHR |  |  |  |  |  |
| 7 | SN | 0.8 | PHR (c) | 10.1 | 15.7 | 28.6 | 43.1 | 57.1 |

(a) Sebacoyl bisbenzoylmethane
(b) Benzoylstearoylmethane
(c) Tin octyl isooctylthioglycolate derivative (IRGASTAB 17MOKS) used as reference.

Clear synergism can be noted between the TGD and the sebacoyl bisbenzoylmethane (SBBM) or benzoylstearoylmethane (BSM). Even with small SBBM quantities (mixture 6) a very high efficiency is obtained, exceeding that of currently used tin compounds.

EXAMPLE 15

Dynamic stability was evaluated at 180° C. on a formulation for rigid transparent articles (No. 1B) using 0.3 PHR of single or mixed organic stabilizers (0.15+0.15 PHR of synergic compounds in mixture). The YI values are given.

|  | Time (minutes) | | | | |
|---|---|---|---|---|---|
|  | 5 | 10 | 15 | 20 | 25 |
| BGD | 17.7 | 19.3 | 21.5 | 28.9 | 60 |
| TGD | 17.5 | 19.1 | 20.1 | 27.3 | 63 |
| BSM | 11.7 | 16.4 | 24.5 | 41.3 | 73.4 |
| SBBM | 10.1 | 13.2 | 22.9 | 33.4 | 68.9 |
| BGD + BSM | 11.0 | 15.2 | 20.3 | 30 | 66 |
| BGD + SBBM | 10 | 12.2 | 16.9 | 30.2 | 68 |
| TGD + BSM | 11.2 | 15.1 | 19.5 | 33 | 68.7 |
| TGD + SBBM | 9.7 | 12.2 | 16.9 | 25.9 | 57.3 |

Synergism can be noted between the compounds of the invention and the betadiketones particularly in maintaining the colour low until burning.

EXAMPLE 16

Thermal stability at 190° C. was evaluated on a formulation for rigid pigmented articles (No. 2) using 0.15 PHR of each organic stabilizer (total 0.3 PHR). The YI values are given.

|  | Time (minutes) | | | | |
|---|---|---|---|---|---|
|  | 1 | 2 | 3 | 4 | 5 |
| without stabilizer | 65.9 | 69 | 71.3 | 74.1 | 74.4 |
| TGD + SBBM | 17.2 | 20.4 | 24.6 | 33.6 | 75.4 |
| BGD + SBBM | 18.4 | 18.7 | 23 | 26 | 35.1 |
| TGM + SBBM | 16.7 | 18.5 | 18.2 | 20.7 | 29.6 |

The very high efficiency of the synergic compositions is noted compared with the PVC mass when stabilized only with primary stabilizers.

EXAMPLE 17

Dynamic stability at 180° C. was evaluated on a PVC/PVA-based formulation for rigid transparent articles (No. 1D) using 0.15 PHR of each organic stabilizer (0.3 PHR in total). The YI values are given.

|  | Time (minutes) | | | |
| --- | --- | --- | --- | --- |
|  | 5 | 10 | 15 | 20 |
| without stabilizer | 24 | 31.1 | 50.2 | 87.7 |
| TGD + SBBM | 7.2 | 9.4 | 23.4 | 65.9 |
| BGD + SBBM | 7.5 | 11 | 31.7 | 83.6 |
| TGM + SBBM | 9.8 | 11 | 30 | 88.6 |

EXAMPLE 18

The test conducted in Example 17 was repeated on a formulation for plasticised transparent articles (No. 3). The YI values are given.

|  | Time (minutes) | | | | | |
| --- | --- | --- | --- | --- | --- | --- |
|  | 5 | 10 | 15 | 20 | 25 | 30 |
| without stabilizer | 10.5 | 14.4 | 18.7 | 19.8 | 17.7 | 28 |
| TGD + SBBM | 7.1 | 7.2 | 7.3 | 8.5 | 13 | 20.3 |
| BGD + SBBM | 7.3 | 7.1 | 7.2 | 8.7 | 13 | 19.5 |
| TGM + SBBM | 8.3 | 7.6 | 7.7 | 8.3 | 12.1 | 18.7 |

The results of Examples 17 and 18 show the high efficiency of the compositions based on the compounds according to the invention in association with betadiketones (in particular bisbetadiketones such as sebacoyl bisbenzoylmethane), both on rigid and on plasticised formulations.

We claim:
1. Compounds of formula (I)

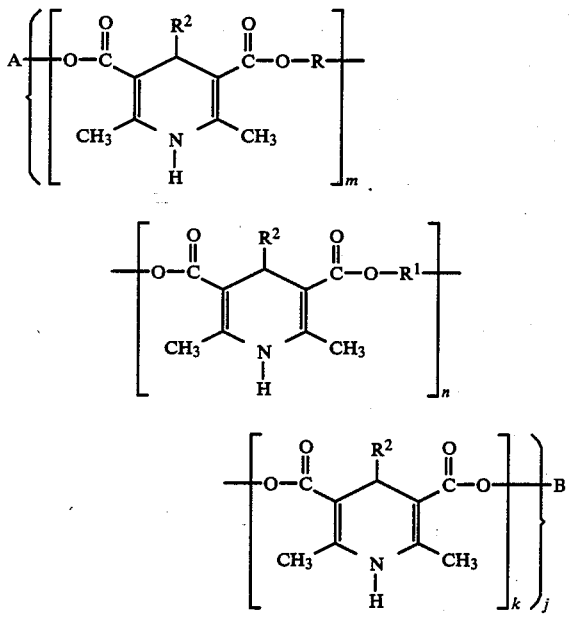

in which:
A represents a linear or branched alkyl of 1-22 C atoms, optionally substituted with one or more groups chosen from alkoxy, alkylthio, hydroxyl optionally esterified with acrylic or alkoxy, alkylthio, hydroxyl optionally esterified with acrylic or methacrylic acid, halogen, aryl; phenyl or aryl of carbocyclic or heterocyclic type optionally substituted with one or more alkyl, alkoxy or halogen groups; alkenyl of 3-10 C atoms; $CH_3COCH_2COO-R-$; $CH_3COCH_2COO-R^1$; $CH_3-C(NH_2)=CH-COOR-$; $CH_3-C(NH_2)=CHCOO-R^1-$; in which the amino group can carry one or more substituents of alkyl, hydroxyalkyl or alkoxyalkyl type or a cyclic substituent of polyalkylene or oxapolyalkylene type, or methylene or a linear or branched alkenyl of 2-22 C atoms;

B can assume the same meaning as A, or can represent a trivalent or polyvalent residue consisting of a linear or branched carbon atom chain optionally carrying substituents of alkoxy, thioalkoxy, aryl, carboxyl or hydroxyl type;

m, n are whole numbers from 0 to 20, the sum of which is at least 2;

k is 0 or 1;

j is a whole number from 1 to 6;

j (k+m+n) is a whole number equal or greater than 2;

R and $R^1$ each independently represent a bivalent hydrocarbon residue, a methylene or phenylene group, or a bivalent residue comprising at least one alkylene group of the type;

$$-(-C_pH_{2p}-X-)_t-C_pH_{2p}$$

in which p is a whole number from 2 to 18, t is a whole number from 0 to 10 and X is oxygen or sulphur, said alkylene group optionally carrying substitutions of alkoxy or thioalkoxy, aryl, carboxyl or hydroxyl type; or R and $R^1$ represent a direct bond with B only if k is 0 and j is greater than 1: $R_2$ represents hydrogen or a monovalent residue of linear or branched alkyl, alkoxycarbonyl.

2. Compounds of formula (I) as claimed in claim 1, characterised in that the sequence of units which are repeated m and n times, where m+n is greater than or equal to 3, are of alternating, block or random type.

3. Compounds of formula (I) as claimed in claim 1, characterised in that:
A, B, which are the same or different, each independently represent a linear or branched $C_1-C_{18}$ alkyl group;
m, k, j=1;
R represents a $-(CH_2)_2-$, $-(CH_2)_4-$ or $-(CH_2)_2-S-(CH_2)_2-$ group;
$R^2$ represents hydrogen.

4. Vinylchloride polymer or copolymer-based compositions containing usual additives, processing auxiliaries and primary stabilizers, comprising as thermal stabilizer at least one compound of formula (I) as defined in claim 1 to the extent of between 0.01% and 3% of the polymer by weight.

5. Compositions as claimed in claim 4, wherein the primary stabilizers include Ca/Zn or Mg/Zn salts of carboxylic acids, organotin mercaptides or carboxylates and their mixtures.

6. Compositions as claimed in claim 4, wherein the additives include betadiketone compounds of formula (II):

$$R^3-CO-CH_2-CO-R^4 \qquad (II)$$

in which:
$R^3$ represents linear or branched $C_1-C_{18}$ alkyl or an aromatic phenyl ring possibly substituted with one or more alkyl, alkoxy or halogen groups;
$R^4$ has the same meaning as $R^3$, independently of $R^3$, or represents a covalent bond, $C_1-C_{18}$ alkylene, polyvalent $C_1-C_{18}$ hydrocarbon, or $-(C_pH_{2p}-X)_t-C_pH_{2p}-$ in which p, t, X have the meanings already given for formula (I), and directly linked to another $-CO-CH_2-CO-R^3$ group.

7. Compositions as claimed in claim 6, wherein the ratio of compounds of formula (I) to betadiketone compounds of formula (II) is between 1:10 and 10:1.

* * * * *